United States Patent [19]

Detty et al.

[11] Patent Number: 5,300,385
[45] Date of Patent: Apr. 5, 1994

[54] AROMATIC HETEROCYCLIC-SUBSTITUTED CYCLIC SULFONE COMPOUNDS AND ELECTROPHOTOGRAPHIC ELEMENTS CONTAINING THEM

[75] Inventors: Michael R. Detty; John A. Sinicropi, both of Rochester; J. Robin Cowdery, Webster; Ralph H. Young, Rochester, all of N.Y.

[73] Assignee: Eastman Kodak Company, Rochester, N.Y.

[21] Appl. No.: 976,911

[22] Filed: Nov. 16, 1992

[51] Int. Cl.⁵ .................. G03G 5/047; G03G 5/06
[52] U.S. Cl. ......................... 430/58; 430/75; 430/76; 430/77; 430/78
[58] Field of Search ............ 430/58, 75, 76, 77, 430/128, 78

[56] References Cited

U.S. PATENT DOCUMENTS

| | | |
|---|---|---|
| 4,514,481 | 4/1985 | Scozzafava et al. |
| 4,927,726 | 5/1990 | Scozzafava et al. ............ 430/58 |
| 4,968,813 | 11/1990 | Rule et al. |
| 5,013,849 | 5/1991 | Rule et al. |
| 5,034,293 | 7/1991 | Rule et al. |
| 5,039,585 | 8/1991 | Rule et al. |

OTHER PUBLICATIONS

Detty et al., *Tetrahedron*, 1985, vol. 41, pp. 4853–4859.

*Primary Examiner*—Christopher Rodee
*Attorney, Agent, or Firm*—Robert Luke Walker

[57] ABSTRACT

Certain chemical compounds, which are aromatic heterocyclic-substituted derivatives of 4H-thiopyran-1,1,-dioxide given by the formula (I) wherein Het is a substituted or unsubstituted heterocyclic ring system containing at least one 5-membered heterocyclic aromatic ring; and R is an alkyl, aralkyl, or cycloalkyl group of 1 to about 10 carbon atoms, or an aryl group of 6 to about 12 carbon atoms, or a substituted or unsubstituted heterocyclic ring system containing at least one 5-membered aromatic heterocyclic ring, are electron-transport agents. These compounds exhibit good speed and toe voltage properties in electrophotographic elements.

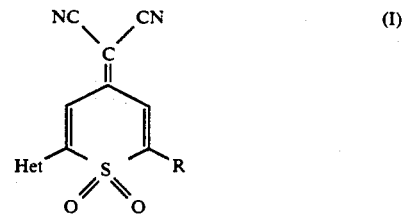

9 Claims, No Drawings

AROMATIC HETEROCYCLIC-SUBSTITUTED CYCLIC SULFONE COMPOUNDS AND ELECTROPHOTOGRAPHIC ELEMENTS CONTAINING THEM

CROSS-REFERENCE TO RELATED APPLICATION

Reference is made to copending, commonly assigned application entitled "Cyclic Sulfone Compounds and Electrophotographic Elements Containing Them", U.S. Ser. No. 07/895,755, filed Jun. 9, 1992.

FIELD OF THE INVENTION

This invention relates to novel aromatic heterocyclic-substituted derivatives of 4H-thiopyran-1,1-dioxide which are useful as electron-transport agents in electrophotographic elements.

BACKGROUND OF THE INVENTION

In electrophotography an image comprising a pattern of electrostatic potential (also referred to as an electrostatic latent image), is formed on a surface of an electrophotographic element comprising at least an insulative photoconductive layer and an electrically conductive substrate. The electrostatic latent image is usually formed by imagewise radiation-induced discharge of a uniform potential previously formed on the surface. Typically, the electrostatic latent image is then developed into a toner image by contacting the latent image with an electrographic developer. If desired, the latent image can be transferred to another surface before development.

In latent image formation the imagewise discharge is brought about by the radiation-induced generation of electron/hole pairs, by a material (often referred to as a charge-generation material) in the electrophotographic element. Depending upon the polarity of the initially uniform electrostatic potential and the type of materials in the electrophotographic element, either the holes or the electrons that have been generated migrate toward the charged surface in the exposed areas and cause the imagewise discharge of the initial potential. What remains is a non-uniform potential constituting the electrostatic latent image.

Many electrophotographic elements are designed to be initially charged with a negative polarity. They contain material, known as a hole-transport agent, which facilitates the migration of positive holes toward the negatively charged surface in imagewise exposed areas. A positively charged toner develops the unexposed areas. Because of the wide use of negatively charging elements, many types of positively charging toners are available. Conversely, relatively few high quality negatively charging toners are available.

For some applications, however, it is desirable to develop the exposed rather than the unexposed surface areas of the element. For example, in laser printing of alphanumeric characters it is more desirable to expose the small surface area that will form visible alphanumeric toner images, rather than waste energy exposing the large background area. In order to accomplish this with available high quality positively charging toners, it is necessary to use an electrophotographic element that is designed to be positively charged. Positive toner can then develop the exposed surface areas (which will have relatively negative electrostatic potential).

An electrophotographic element designed to be initially positively charged, however, preferably contains an electron-transport agent, i.e., a material which facilitates the migration of photogenerated electrons toward the positively charged surface. Unfortunately, many good hole-transport agents are available, but relatively few electron transport agents are known.

A number of chemical compounds having electron-transport properties are described, for example, in U.S. Pat. Nos. 4,175,960; 4,474,865; 4,559,287; 4,606,861; and 4,609,602. U.S. Pat. No. 4,514,481 discloses 4H-thiopyran-1,1-dioxide compounds as electron-transport agents and illustrates incorporating them in polymeric binder layers of electrophotographic elements. Unsymmetrically substituted 2,6-diaryl-4H-thiopyran-1,1-dioxide compounds are disclosed in U.S. Pat. Nos. 4,968,813, 5,013,849, 5,034,293, and 5,039,585.

Many electron-transport agents of the prior art have one or more drawbacks. Many do not perform the electron-transporting function well under certain conditions or in certain types of electrophotographic elements. Many agents require high exposure to discharge the surface potential of a charged electrophotographic element, resulting in low electrophotographic speed. Many agents also cause a high residual voltage to remain on the surface of the element after discharge, resulting in increased background density in the copy.

Thus, there is a continuing need for electrophotographic elements containing new chemical compounds that lower the amount of exposure required to discharge the surface potential of the charged elements, leading to increased electrophotographic speed. There is also a continuing need for electrophotographic elements containing compounds that lower the residual, or toe, voltage remaining on the surface after discharge. The present invention meets these needs.

SUMMARY OF THE INVENTION

The present invention provides new chemical compounds having utility as electron-transport agents. The new compounds are aromatic heterocyclic-substituted derivatives of 4H-thiopyran-1,1-dioxide having the structure

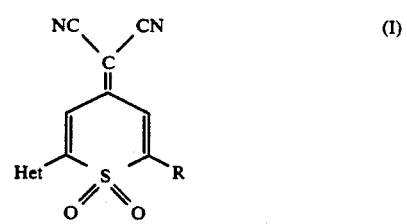

where Het is a substituted or unsubstituted heterocyclic ring system containing at least one 5-membered aromatic heterocyclic ring, and R is an alkyl, aralkyl, or cycloalkyl group of 1 to about 10 carbon atoms, or an aryl group of 6 to about 12 carbon atoms, or a substituted or unsubstituted heterocyclic ring system containing at least one 5-membered aromatic heterocyclic ring.

The novel compounds of structure (I) exhibit good electrophotographic speed and toe voltage properties in elements of the invention.

DETAILED DESCRIPTION OF THE INVENTION

In the novel 4H-thiopyran-1,1-dioxide compounds of structure (I), Het is a substituted or unsubstituted heterocyclic ring system containing at least one 5-membered aromatic heterocyclic ring. Examples of such ring systems are: 2-thienyl, 3-thienyl, 2-thianaphthenyl, 2-furanyl, 3-furanyl, 2-benzofuranyl, 2-pyrrolyl, 1-methyl-2-pyrrolyl, 3-pyrrolyl, 1-ethyl-2-indolyl, 1-isopropyl-3-indolyl, 2-thiazolyl, 5-methyl-2-benzothiazolyl, 2-oxazolyl, 5-chloro-2-benzoxazolyl, 2-selenophenyl, 2-tellurophenyl, and the like.

In the compounds of structure (I), R is an alkyl, aralkyl, or cycloalkyl group of 1 to about 10 carbon atoms, or an aryl group of 6 to about 12 carbon atoms, or a heterocyclic ring system containing at least one 5-membered aromatic heterocyclic ring. The group can be substituted or unsubstituted. Examples of unsubstituted alkyl groups are methyl, ethyl, propyl, isopropyl, butyl, isobutyl, t-butyl, pentyl, hexyl, 2-ethylhexyl, octyl, and the like. Aralkyl groups can be benzyl, phenethyl, and the like. Cycloalkyl groups can be cyclopentyl, cyclohexyl, 4-methylcyclohexyl, and the like. For substituted alkyl and cycloalkyl groups, substituents can be alkoxy, aryloxy, and the like. For substituted aralkyl groups, substituents can be alkyl, alkoxy, halo, and the like.

Aryl groups can be phenyl, naphthyl, and the like. For substituted aryl groups, substituents can be alkyl, alkoxy, halo, nitro, and the like. Heterocyclic ring systems containing at least one 5-membered aromatic heterocyclic ring are as defined above for Het. Where both Het and R represent aromatic heterocyclic groups, the groups can be the same or different.

The unsymmetrically substituted 4H-thiopyran-1,1-dioxide compounds of the present invention can be prepared from 1,5-disubstituted-1,4-pentadiyn-3-ones by the following scheme:

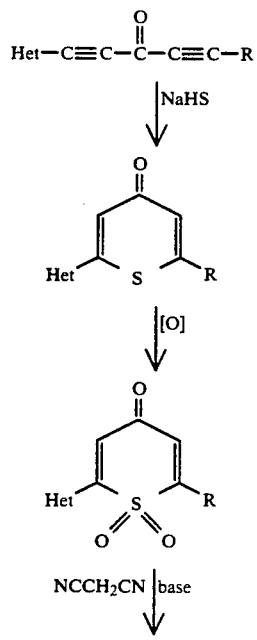

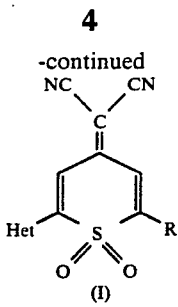

A route to unsymmetrical 1,5-disubstituted 1,4-pentadiyn-3-ones is described by Detty et al., *J. Org. Chem.*, 1987, Vol. 52, pp. 3662–3668. The reaction of substituted 1,4-pentadiyn-3-ones with sodium hydrosulfide to produce 1-thiopyran-4-ones is described by Detty et al., *Tetrahedron*, 1985, Vol. 41, pp. 4853–4859. Conversion of thiopyranones to the corresponding 1,1-dioxides by oxidizing agents such as peracetic acid and reaction of the dioxides with malonitrile under basic conditions are disclosed in U.S. Pat. No. 4,514,481, incorporated herein by reference.

Unsymmetrically substituted 1,4-pentadiyn-3-ones in which R is alkyl, aralkyl, or cycloalkyl can be synthesized by the reaction of alkyl-, aralkyl-, or cycloalkyl-substituted alkynyl lithium compounds with heterocyclic-substituted propargyl aldehydes to yield 1,4-pentadiyn-3-ols, which are then oxidized by reagents such as chromic acid to the corresponding diynones. This is illustrated by Scheme A, as follows:

Scheme A

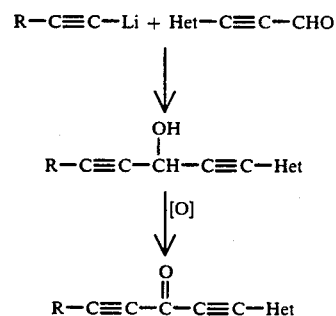

Heterocyclic-substituted propargyl aldehydes can be prepared via propiolic esters from tetrachlorocyclopropene and a heterocyclic compound according to the following scheme:

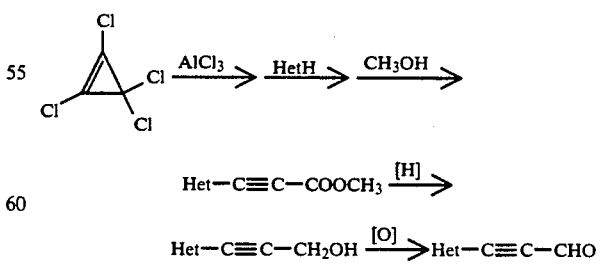

The reduction of propiolic esters to propargyl alcohols can be effected by hydride reducing agents, for example, diisobutylaluminum hydride. For oxidation of propargyl alcohols to the corresponding aldehydes, pyridinium chlorochromate is a suitable reagent.

Unsymmetrically substituted 4H-thiopyran-4-one-1,1-dioxide compounds required to prepare electron-transport agents of structure (I) in which R is aryl or heterocyclyl can be synthesized by the following sequence of reactions: 1) base-catalyzed condensation of a heterocyclic aldehyde and a 4-aryl- or 4-heterocyclyl-3-buten-2-one to produce a 1,5-disubstituted-1,4-pentadien-3-one; 2) cycloaddition of hydrogen sulfide to yield a 1,5-disubstituted tetrahydrothiopyran-4-one; 3) oxidation by a peracid to the corresponding tetrahydrothiopyran-4-one-1,1-dioxide; and 4) further oxidation by a mixture of iodine, concentrated sulfuric acid, and dimethylsulfoxide to the substituted 4H-thiopyran-4-one-1,1-dioxide. The latter compound is converted to the 4-dicyanomethylene derivative, as previously described.

This synthetic sequence is depicted in Scheme B, shown below.

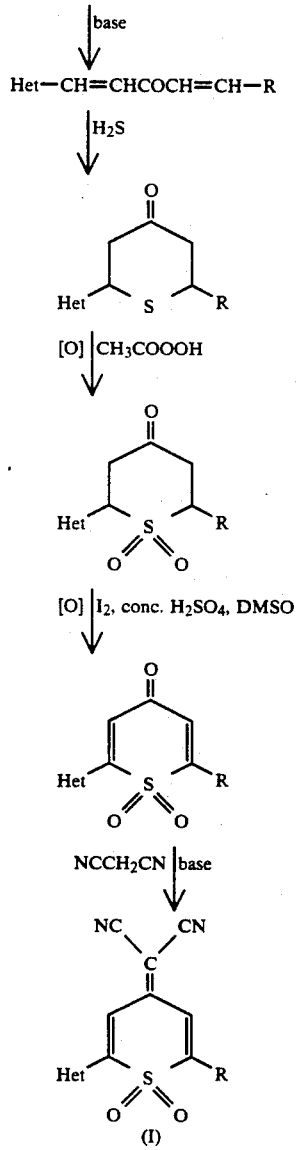

Symmetrically disubstituted 1,4-pentadien-3-ones used in the preparation of compounds of the invention in which Het and R are the same can be synthesized by the base-catalyzed condensation of two molar equivalents of a heterocyclic aldehyde with one of acetone, as follows:

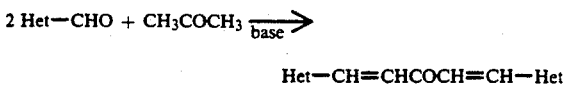

The remainder of the synthetic sequence is as shown in Scheme B above.

Shown below are formulas of new chemical compounds that are useful as electron-transport agents in electrophotographic elements of the present invention.

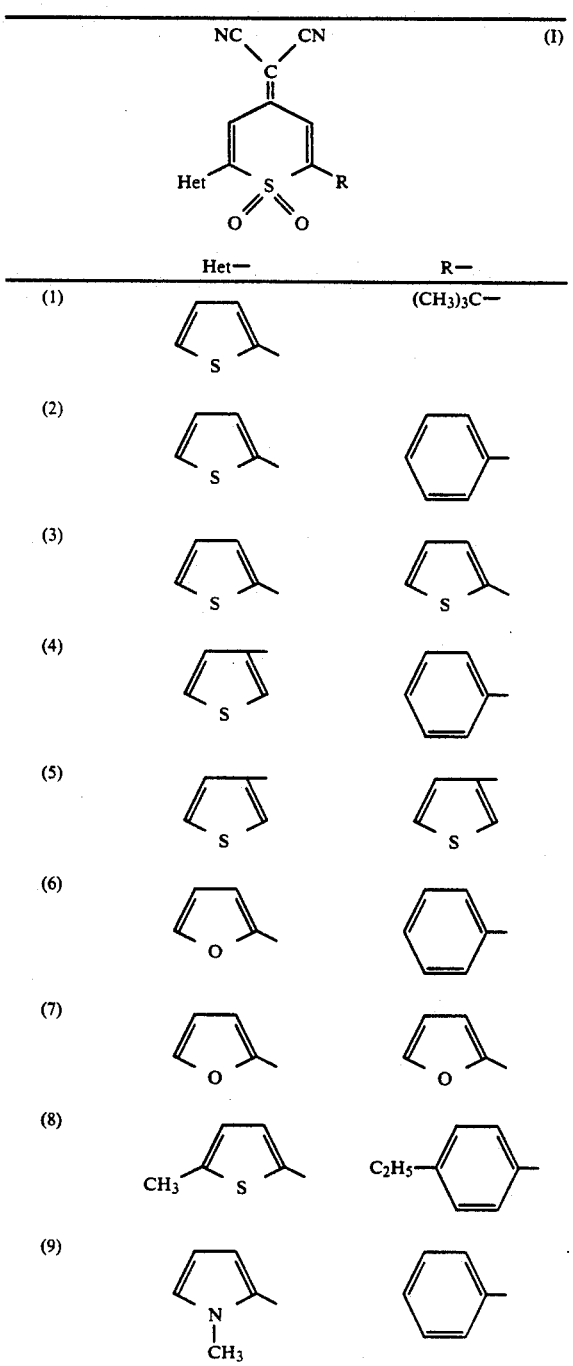

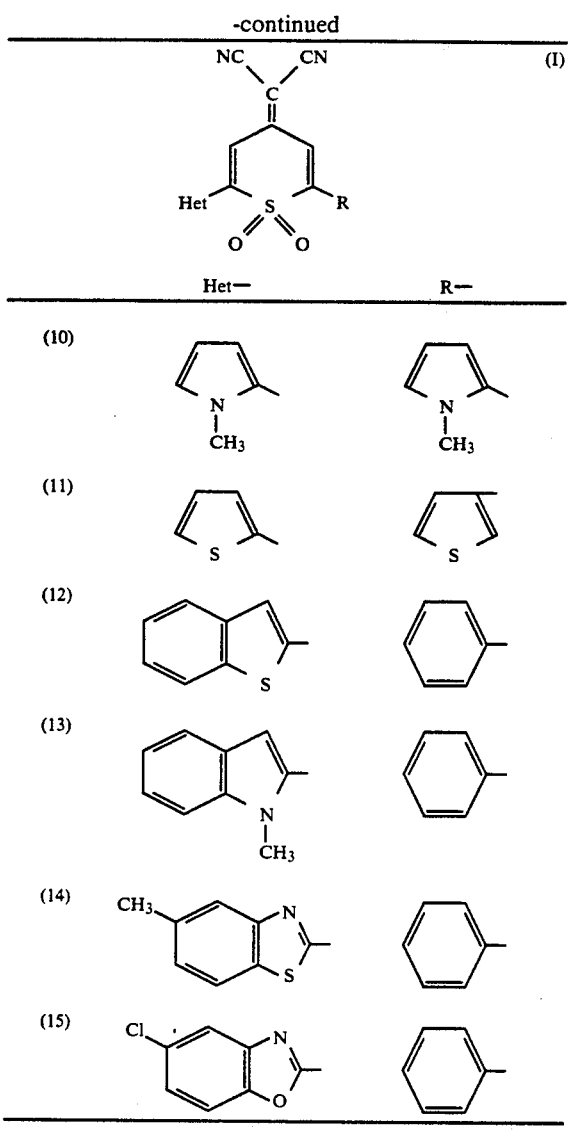

The new electrophotographic elements of the invention can be of various types, all of which contain one or more of the chemical compounds of structure (I) described above to serve as electron-transport agents in the elements. The various types of elements in accordance with the present invention include both those commonly referred to as single layer or single-active-layer elements and those commonly referred to as multiactive, multilayer, or multi-active-layer elements.

Single-active-layer elements are so named because they contain only one layer that is active both to generate and to transport charges in response to exposure to actinic radiation. Such elements typically comprise at least an electrically conductive layer in electrical contact with a photoconductive layer. In single-active-layer elements of the invention, the photoconductive layer contains a charge-generation material to generate electron/hole pairs in response to actinic radiation and an electron-transport material, comprising one or more of the chemical compounds of structure (I) described above, which is capable of accepting electrons generated by the charge-generation material and transporting them through the layer to effect discharge of the initially uniform electrostatic potential. The photoconductive layer is electrically insulative except when exposed to actinic radiation, and it sometimes contains an electrically insulative polymeric film-forming binder, which may itself be the charge-generating material, or it may be an additional material that is not charge-generating. In either case, the electron-transport agent is dissolved or dispersed as uniformly as possible in the binder film.

Multiactive elements are so named because they contain at least two active layers, at least one of which is capable of generating charge (i.e., electron/hole pairs) in response to exposure to actinic radiation and is therefore referred to as a charge-generation layer (CGL), and at least one of which is capable of accepting and transporting charges generated by the charge-generation layer and is therefore referred to as a charge-transport layer (CTL). Such elements typically comprise at least an electrically conductive layer, a CGL, and a CTL. Either the CGL or the CTL is in electrical contact with both the electrically conductive layer and the remaining CTL or CGL. The CGL contains at least a charge-generation material; the CTL contains at least a charge-transport agent; and either or both layers can contain an electrically insulative film-forming polymeric binder. In multiactive elements of the invention, the charge-transport agent is an electron-transport agent comprising at least one of the chemical compounds of structure (I) described above.

Single-active-layer and multiactive electrophotographic elements and their preparation and use in general, are well known and are described in more detail, for example, in U.S. Pat. Nos. 4,701,396; 4,666,802; 4,578,334; 4,719,163; 4,175,960; 4,514,481; and 3,615,414, the disclosures of which are incorporated herein by reference.

In preparing single-active-layer electrophotographic elements of the invention, the components of the photoconductive layer, including any desired addenda, can be dissolved or dispersed together in a liquid and can be coated on an electrically conductive layer, or support. The liquid is then allowed or caused to evaporate from the mixture to form the permanent layer, which contains from about 10 to about 70 weight percent of the electron-transport agent and from 0.01 to about 50 weight percent of the charge-generating material. Included among many useful liquids for this purpose are, for example, aromatic hydrocarbons such as benzene, toluene, xylene and mesitylene; ketones such as acetone and butanone; halogenated hydrocarbons such as dichloromethane, trichloroethane, chloroform, and ethylene chloride; ethers, including ethyl ether and cyclic ethers such as tetrahydrofuran; other solvents such as acetonitrile and dimethylsulfoxide; and mixtures thereof.

In preparing multiactive electrophotographic elements of the invention, the components of the CTL can be similarly dissolved or dispersed in such a liquid coating vehicle and can be coated on either an electrically conductive layer or support, or on a CGL previously similarly coated or otherwise formed on the conductive layer or support. In the former case, a CGL is thereafter coated or otherwise formed (e.g., by vacuum-deposition) on the CTL. The CTL will usually contain from about 10 to about 70 weight percent of electron-transport agent, although concentrations outside that range may be found to be useful in some cases.

The CTL of a multiactive electrophotographic element can also, in accordance with the present invention, be applied by other means such as vacuum deposition to a CGL coated on a conductive support. A vacuum-deposited CTL can contain 100 weight percent of the electron-transport agent and can be very thin, with a thickness of about 1 to about 10 μm, preferably about 2 to about 4 μm.

Various electrically conductive layers or supports can be employed in electrophotographic elements of the invention, for example, paper (at a relative humidity above 20 percent); aluminum-paper laminates; metal foils such as aluminum foil, zinc foil, etc.; metal plates such as aluminum, copper, zinc, brass and galvanized plates; vapor deposited metal layers such as silver, chromium, vanadium, gold, nickel, aluminum and the like; and semiconductive layers such as cuprous iodide and indium tin oxide. The metal or semiconductive layers can be coated on paper or conventional photographic film bases such as poly(ethylene terephthalate), cellulose acetate, polystyrene, etc. Such conducting materials as chromium, nickel, etc. can be vacuum-deposited on transparent film supports in sufficiently thin layers to allow electrophotographic elements so prepared to be exposed from either side.

Any charge-generation material can be utilized in elements of the invention. Such materials include inorganic and organic (including monomeric organic, metallo-organic and polymeric organic) materials, for example, zinc oxide, lead oxide, selenium, or phthalocyanine, perylene, arylamine, polyarylalkane, and polycarbazole materials, among many others.

In solvent-coating a photoconductive layer of a single-active-layer element or a CGL and/or CTL of a multiactive element of the invention, a film-forming polymeric binder can be employed. The binder may, if it is electrically insulating, help provide the element with electrically insulating characteristics. It also is useful in coating the layer, in adhering the layer to an adjacent layer, and, when it is a top layer, in providing a smooth, easy to clean, wear-resistant surface.

Representative materials which can be employed as binders in charge-generation and charge-transport layers are film-forming polymers having a fairly high dielectric strength and good electrically insulating properties. Such binders include, for example, styrene-butadiene copolymers; vinyltoluene-styrene copolymers; styrene-alkyd resins; silicone-alkyd resins; soya-alkyd resins; vinylidene chloride-vinyl chloride copolymers; poly(vinylidene chloride); vinylidene chloride-acrylonitrile copolymers; vinyl acetate-vinyl chloride copolymers; poly(vinyl acetals), such as poly(vinyl butyral); nitrated polystyrene; poly(methylstyrene); isobutylene polymers; polyesters, such as poly[ethylene-co-alkylenebis(alkyleneoxyaryl)phenylenedicarboxylate]; phenol-formaldehyde resins; ketone resins; polyamides; polycarbonates; polythiocarbonates; poly[ethylene-coisopropylidene-2,2-bis(ethyleneoxyphenylene)terephthalate]; copolymers of vinyl haloacrylates and vinyl acetate; chlorinated polyolefins such as chlorinated polyethylene; and polyimides, such as poly[1,1,3-trimethyl-3-(4'-phenyl)-5-indane pyromellitimide].

Polymeric binders should provide little or no interference with the generation or transport of charges in the layer. Examples of binders which are especially useful include bisphenol A polycarbonates and polyesters such as poly[(4,4'-norbornylidene)diphenylene terephthalate-co-azelate].

CGL's and CTL's in elements of the invention can also optionally contain other addenda such as leveling agents, surfactants, plasticizers, sensitizers, contrast-control agents, and release agents, as is well known in the art.

Also, elements of the invention can contain any of the optional additional layers known to be useful in electrophotographic elements in general, for example, subbing layers, overcoat layers, barrier layers, and screening layers.

The following preparations and examples are presented to further illustrate some specific electrophotographic elements of the invention and chemical compounds useful as electron-transport agents therein.

EXAMPLE 1

Synthesis of 4-dicyanomethylene-2-(2-thienyl)-6-t-butyl-4H-thiopyran-1,1-dioxide (Compound 1)

The procedures given below are representative of those used in synthesis Scheme A to prepare unsymmetrically substituted electron-transfer agents of the present invention.

Synthesis of 1-(2-thienyl)-5-t-butyl-1,4-pentadiyn-3-one. Lithium t-butylacetylide was prepared by the dropwise addition of 1.6M n-butyl lithium (1.0 equivalent) in hexane to a 1.5M solution of t-butylacetylene (1.2 equivalents) in anhydrous tetrahydrofuran cooled to 0° C. under an argon atmosphere. A 1.5M solution of (2-thienyl)propargyl aldehyde (1.0 equivalent, prepared as described in Detty et al., *J Org. Chem.*, 1987, Vol. 52, pp. 3662–3668) in anhydrous tetrahydrofuran was added dropwise. The mixture was stirred for one hour longer while it warmed to ambient temperature, then poured into cold 10% aqueous HCl. The product was extracted with ether, and the ether extracts were washed with brine, dried over $Na_2SO_4$, and concentrated to a residual oil, which was used without further purification.

A 10% solution of chromic acid was prepared by the addition of 29.8 g (0.100 mol) of sodium dichromate dihydrate to a stirred solution of 40 g of sulfuric acid in 180 g of ice. The resulting solution was stirred for 1.5 hours prior to use; then a 10% molar excess of this solution was added dropwise to the diynol obtained as described above, which was dissolved in an equal volume of acetone and cooled to 0° C. After completion of addition, the mixture was stirred for one hour at ambient temperature, then diluted with an equal volume of water. The product was extracted with ether, and the ether extracts were washed with brine, dried over $Na_2SO_4$, and concentrated to give 1-(2-thienyl)-5-t-butyl-1,4-pentadiyn-3-one in 71% overall yield as a yellow oil. $^1H$ NMR, IR, and field desorption mass spectral (FDMS) analyses were consistent with the expected structure.

Synthesis of 2-(2-thienyl)-6-t-butyl-4H-thiopyran-4-one. The diynone prepared as described above was dissolved in isopropyl alcohol to give a 0.5M solution. A 1.0M solution of sodium hydrogen sulfide dihydrate (1.5 equivalents) in saturated aqueous sodium bicarbonate was prepared and then diluted with an equal volume of distilled water. The aqueous solution was slowly added, with good stirring, to the diynone solution. After completion of addition, the mixture was stirred for one hour at ambient temperature, then diluted with an equal volume of water. The product was extracted with dichloromethane, and the extracts were washed with brine, dried over $Na_2SO_4$, and concentrated. The residue was purified by chromatography on silica gel, with elution by 25% ethyl acetate in dichloromethane. 2-(2-Thienyl)-6-t-butyl-4H-thiopyran-4-one was obtained in 23% yield as a red oil. $^1$H NMR, IR, and FDMS analyses were consistent with the proposed structure.

Synthesis of 2-(2-thienyl)-6-t-butyl-4H-thiopyran-4-one-1,1-dioxide. To a 1.0M solution in ethyl acetate of the thiopyranone obtained as described above was added a 35% solution of peracetic acid (5 equivalents) in acetic acid. The resulting solution was heated at reflux for 3 hours, then poured into water. The product was extracted with three portions of ethyl acetate, and the combined extracts were washed successively with 10% aqueous sodium bisulfite (3 times), saturated aqueous sodium bicarbonate (3 times), and brine, dried over $Na_2SO_4$, and concentrated. The residue was chromatographed on silica gel, with elution by dichloromethane. There was obtained a 39% yield of 2-(2-thienyl)-6-t-butyl-4H-thiopyran-4-one-1,1-dioxide as a yellow oil. $^1$H NMR, IR, and FDMS analyses were consistent with the proposed structure.

Synthesis of 4-dicyanomethylene-2-(2-thienyl)-6-t-butyl-4H-thiopyran-1,1-dioxide. A mixture of 1.32 g (4.00 mmol) of the thiopyranone dioxide obtained a described above, 0.33 g (5.0 mmol) of malononitrile, and 5.0 g of basic alumina in 50 mL of dichloromethane was stirred at ambient temperature for 15 hours. The mixture was concentrated, and the residue was chromotographed on silica gel, using dichloromethane as eluent. 4-Dicyanomethylene-2-(2-thienyl)-6-t-butyl-4H-thiopyran-1,1-dioxide was obtained in 30% yield as a yellow crystalline solid, m.p. 163.5°–165° C. $^1$H NMR, IR, and FDMS analyses were consistent with the proposed structure.

EXAMPLE 2

Synthesis of 4-dicyanomethylene-2-(2-thienyl)-6-phenyl-4H-thiopyran-1,1-dioxide (Compound 4)

The procedures given below are representative of those used in synthesis Scheme B to prepare unsymmetrically substituted electron-transport agents of the present invention.

Synthesis of E,E-1-(2-thienyl)-5-phenyl-1,4-pentadien-3-one. A mixture of 65.1 g (0.45 mol) of E-4-phenyl-3-buten-2-one, 50 g (0.45 mol) of 2-thiophenecarboxaldehyde, 4 mL of aqueous 10% sodium hydroxide, 50 mL of water, and 75 mL of ethanol was stirred at ambient temperature for 15 hours. The solid which separated was collected by filtration and air dried to give 85.6 g (80% yield) of E,E-1-(2-thienyl)-5-phenyl-1,4-pentadien-3-one as a yellow solid. $^1$H NMR, IR, and FDMS analyses were consistent with the expected structure.

Synthesis of 2,3,5,6-tetrahydro-2-(2-thienyl)-6-phenyl-thiopyran-4-one. A mixture of 85.0 g (0.35 mol) of the dienone prepared as described above, 8 g of anhydrous sodium acetate, 50 mL of dimethylformamide, and 400 mL of ethanol was placed in a flask equipped with a mechanical stirrer, reflux condenser, and gas inlet tube and heated to boiling on a steam bath. Hydrogen sulfide gas was slowly bubbled into the mixture until all the dienone had been consumed. The mixture was cooled to ambient temperature and diluted with 2 L of water. The product was extracted with 4 300-mL portions of dichloromethane. The combined extracts were washed with brine, dried over $MgSO_4$, and concentrated. There was obtained 85.3 g (86% yield) of 2,3,5,6-tetrahydro-2-(2-thienyl)-6-phenyl-thiopyran-4-one as a solid mixture of diastereoisomers. $^1$H NMR, IR, and FDMS analyses were consistent with the proposed structure.

Elemental analysis: Calcd for $C_{15}H_{14}OS_2$: C,58.80; H,4.61. Found: C,58.87; H, Synthesis of 2,3,5,6-tetrahydro-2-(2-thienyl)-6-phenyl-thiopyran-4-one-1,1-dioxide. To a stirred mixture of 41.3 g (0.15 mol) of the tetrahydrothiopyranone prepared as described above, 8 g of anhydrous sodium acetate, and 500 mL of dichloromethane was added dropwise 225 mL of 30% peracetic acid in acetic acid. After completion of addition, the mixture was stirred for one hour longer at ambient temperature. To the mixture was added 500 mL of water. The aqueous phase was separated and extracted with an additional 300 mL of dichloromethane. The dichloromethane solutions were combined, washed with dilute aqueous sodium hydroxide, dried over $MgSO_4$, and concentrated. There was obtained 42.6 g (92% yield) of 2,3,5,6-tetrahydro-2-(2-thienyl)-6-phenyl-thiopyran-4-one-1,1-dioxide as an oily solid. $^1$H NMR, IR, and FDMS analyses were consistent with the proposed structure.

Synthesis of 2-(2-thienyl)-6-phenyl-4H-thiopyran-4-one-1,1-dioxide. A mixture of 42.5 g (0.14 mol) of the tetrahydrothiopyranone dioxide obtained as described above, 250 mL of dimethylsulfoxide, 7.5 g of iodine, and 4 mL of concentrated sulfuric acid was stirred and heated on a steam bath for 4 hours. After cooling to ambient temperature, the mixture was diluted with one L of water. The product was extracted with 4 500-mL portions of dichloromethane. The extracts were combined, washed with brine, dried over $MgSO_4$, and concentrated. The residue was slurried with ethanol, and the resulting solid was collected by filtration and dried to give 37.5 g (89% yield) of 2-(2-thienyl)-6-phenyl-4H-thiopyran-4-one-1,1-dioxide as a dark solid, m.p. 162.5°–163.5° C. IR and FDMS analyses were consistent with the proposed structure. Elemental analysis: Calcd for $C_{15}H_{10}O_3S_2$: C,59.58; H,3.33. Found: C,59.90; H,3.68.

Synthesis of 4-dicyanomethylene-2-(2-thienyl)-6-phenyl-4H-thiopyran-1,1-dioxide. A mixture of 50.0 g (0.165 mol) of the thiopyranone dioxide prepared as described above, 20.0 g (0.30 mol) of malononitrile, and 250 mL of ethanol was stirred and heated at reflux. To this mixture was added dropwise a solution of 0.50 mL of piperidine in 30 mL of ethanol. After 4 hours at reflux, the mixture was cooled to ambient temperature. The solid that separated was collected by filtration and washed with ethanol, then treated with a boiling mixture of ethyl acetate and ethanol, and again collected. There was obtained 37.2 g (64% yield) of 4-dicyanomethylene-2-(2-thienyl)-6-phenyl-4H-thiopyran-1,1-dioxide as an orange solid, m.p. 214°–232° C. $^1$H NMR, IR, and FDMS analyses were consistent with the proposed structure. Elemental analysis: Calcd for $C_{18}H_{10}N_2O_2S_2$: C, 61.70; H, 2.88; N, 7.99; S, 18.30. Found: C, 61.28; H, 2.97; N, 7.93; S, 18.27.

EXAMPLE 3

Synthesis of 4-dicyanomethylene-2,6-di-(3-thienyl)-4H-thiopyran-1,1-dioxide (Compound 5)

The procedures given below are representative of those used to prepare symmetrically substituted electron-transport agents of the present invention.

Synthesis of E,E-1,5-di-(3-thienyl)-1,4-pentadien-3-one. A mixture of 29.8 g (0.27 mol) of 3-thiophenecarboxaldehyde, 7.7 g (0.13 mol) of acetone, 80 mL of ethanol, 40 mL of water, and 2 mL of 10% aqueous sodium hydroxide was stirred for 15 hours at ambient temperature. The solid that crystallized from the mixture was collected by filtration, and is dried to give 29.2 g (46% yield) of E,E-1,5-di-(3-thienyl)-1,4-pentadien-3-one as a yellow solid. $^1$H NMR, IR, and FDMS analyses were consistent with the expected structure. Elemental analysis: Calcd for $C_{13}H_{10}OS_2$: C, 63.38; H, 4.09. Found: C, 63.10; H, 4.12.

Synthesis of 2,3,5,6-tetrahydro-2,6-di-(3-thienyl)-thiopyran-4-one. A mixture of 40.0 g (0.16 mol) of the dienone prepared as described above, 5 g of anhydrous sodium acetate, 30 mL of dimethylformamide, and 150 mL of ethanol was placed in a flask equipped with a mechanical stirrer, reflux condenser, and gas inlet tube and heated to boiling on a steam bath. Hydrogen sulfide gas was slowly bubbled into the mixture until all the dienone had been consumed. The mixture was cooled to ambient temperature and diluted with one L of water. The product was extracted with 4 250-mL portions of dichloromethane. The combined extracts were combined, washed with brine, dried over $MgSO_4$ and concentrated. There was obtained 28.3 g (62% yield) of 2,3,5,6-tetrahydro-2,6-di-(3-thienyl)-thiopyran-4-one as an oil, which was not further purified. FDMS analysis of this oil was consistent with the expected structure.

Synthesis of 2,3,5,6-tetrahydro-2,6-di-(3-thienyl)-thiopyran-4-one-1,1-dioxide. To a stirred mixture of 27.3 g (0.098 mol) of the tetrahydrothiopyranone obtained as described above, 5 g of anhydrous sodium acetate, and 300 mL of dichloromethane was added dropwise 140 mL of 30% peracetic acid in acetic acid. After addition was complete, the mixture was stirred for one hour at ambient temperature, then diluted with 500 mL of water. The aqueous phase was separated and extracted with 300 mL of dichloromethane. The dichloromethane solutions were combined, washed with dilute aqueous sodium hydroxide, dried over $MgSO_4$, and concentrated. There was obtained 28.3 g (93% yield of 2,3,5,6-tetrahydro-2,6-di-(3-thienyl)-thiopyran-1,1-dioxide as an oil, which was not further purified. FDMS analysis of this oil was consistent with the proposed structure.

Synthesis of 2,6-di-(3-thienyl)-4H-thiopyran-4-one-1,1-dioxide. A mixture of 28.3 g (0.091 mol) of the tetrahydrothiopyranone dioxide obtained as described above, 100 mL of dimethylsulfoxide, 5 g of iodine, and 2 mL of concentrated sulfuric acid was stirred and heated on a steam bath for 2 hours. After cooling to ambient temperature, the mixture was diluted with one L of water. The product was extracted with 4 500-mL portions of dichloromethane. The combined extracts were washed with brine, dried over $MgSO_4$, and concentrated. The residue was slurried with ethanol to give a solid, which was collected by filtration and dried. There was obtained 27.5 g (90% yield) of 2,6-di-(3-thienyl)-4H-thiopyran-1,1-dioxide as a dark solid, m.p. 162.5°-163.5° C. $^1$H NMR, IR, and FDMS analyses were consistent with the proposed structure.

Elemental analysis: Calcd for $C_{13}H_8O_3S_3$: C, 50.63; H, 2.61. Found: C, 50.38; H, 2.35

Synthesis of 4-dicyanomethylene-2,6-di-(3-thienyl)-4H-thiopyran-1,1-dioxide. A mixture of 26.3 g (0.085 mol) of the thiopyranone dioxide prepared as described above, 16.4 g (0.25 mol) of malononitrile, and 150 mL of ethanol was stirred and heated at reflux. To this mixture was added dropwise a solution of 0.25 mL of piperidine in 40 mL of ethanol. After 4 hours at reflux, the mixture was cooled to ambient temperature. The solid that crystallized from the mixture was collected by filtration and washed with ethanol, then treated with a boiling mixture of ethyl acetate and ethanol, and again collected. There was obtained 25.2 g (83% yield) of 4-dicyanomethylene-2,6-di-(3-thienyl)-4H-thiopyran-1,1-dioxide as an orange crystalline solid, m.p. 275°-285° C. $^1$H NMR, IR, and FDMS analyses were consistent with the proposed structure.

Elemental analysis: Calcd for $C_{16}H_8N_2O_2S_3$: C, 53.92; H, 2.26; N, 7.86; S, 26.99. Found: C, 54.08; H, 2.38; N, 8.01; S, 26.14.

The structure, preparation, and measurement of performance of electrophotographic elements within the scope of the invention are described below. Electrophotographic sensitivity of the elements of the invention was demonstrated by electrostatically corona-charging them to an initial positive potential, then exposing them to actinic radiation (radiation having peak intensity at a wavelength to which the charge-generation material in the elements is sensitive in order to generate electron-hole pairs) in amounts sufficient to discharge 50% of the initial voltage. Electrophotographic sensitivity was measured in terms of the amount of incident actinic radiant energy (expressed in ergs/cm$^2$) needed to discharge the initial voltage down to the desired level. The lower the amount of radiation needed to achieve the desired degree of discharge, the higher is the electrophotographic sensitivity, or speed, of the element, and vice versa.

In illustrating dark decay properties, the rate of discharge of the initial voltage, expressed in volts/second (V/s), was measured while the elements remained in darkness, i.e., before any exposure to actinic radiation. This was accomplished by measuring the time required for the voltage of the element to decrease from, for example, an initial value of 80 volts down to 60 volts and calculating the rate of dissipation therefrom. The lower the rate of discharge in darkness, the better is the dark decay property of the elements, i.e., the better their ability to retain their initial potential before exposure.

In the tables of performance data in the following examples, "Electron-transport agent" refers to the chemical compound incorporated in the CTL of an electrophotographic element to serve as an electron-transport agent. "$V_o$" refers to the uniform positive potential in volts on the surface of the elements, after they were charged by corona-charging and after any dark decay, such potential having been measured just prior to any exposure of the elements to actinic radiation. "E (50% $V_o$)" refers to the amount of incident actinic radiant energy, expressed in ergs/cm$^2$, needed to discharge 50% of $V_o$. "DD" refers to the rate of dark decay of the elements, prior to exposure to actinic radiation, measured in volts/second (V/s) as described above. The toe voltage, "$V_{toe}$", refers to the final potential in volts remaining on the surface of the element after discharge.

EXAMPLE 4

Structure, preparation, and performance of electrophotographic elements from compounds (2), (3), (4), (5), (6) and (7)

Electrophotographic elements of the invention containing new electron-transport agents in the CTL were prepared by the following procedure:

A thin conductive layer of aluminum was vacuum-deposited on a 178 μm-thick film of polyethylene terephthalate. The aluminum-coated film was then overcoated by electron-beam evaporation with a 500-angstrom-thick layer of silicon dioxide prior to application of a charge-generation layer.

A charge-generation layer (CGL) was prepared by dispersing 2 parts by weight of titanyl tetrafluorophthalocyanine (described in U.S. Pat. No. 4,701,396), a charge-generation material, in a solution of 1 part by weight of a polymeric binder, comprising a polyester formed from 4,4'-(2-norbornylidene)-diphenol and terephthalic acid: azelaic acid (40:60 molar ratio) in dichloromethane containing a small amount of DC-510 ® siloxane coating aid (from Dow Corning), ball milling the dispersion, diluting with a mixture of dichloromethane and 1,1,2-trichloroethane to achieve suitable coating viscosity, coating the dispersion on the conductive layer, and evaporating the solvent to yield a CGL of 0.6 μm thickness.

A charge-transport layer (CTL) was applied on the CGL coated on the conductive support by vacuum deposition of electron-transport agents of the invention, compounds (2), (3), (4), (5), (6) and (7). The rate of deposition was maintained at least than 30 angstroms per second, and the thickness of the resulting CTL was 2.0 μm.

A control coating was prepared and coated in the same manner, using the electron-transport agent 4-dicyanomethylene-2-phenyl-6-(4-tolyl)-4H-thiopyran-1,1-dioxide (Compound I-A of U.S. Pat. No. 5,013,849), which is not of the invention.

Six hours after deposition of the CTL, each of the electrophotographic elements so prepared was corona-charged to a uniform positive potential. Each element was subjected to simulated imaging exposure by exposing it at a rate of 2 ergs per cm² of element surface per second through the outer surface of the CTL to radiation at a wavelength of about 680 nm, thus generating electron/hole pairs in the CGL, and then measuring the values for E(50% $V_o$).

The dark decay rate for each element was determined from the measurement of the time required for the surface voltage to drop from 80 to 60 volts and, in one instance, from 30 to 20 volts in darkness.

The toe voltage was determined by measuring the potential remaining on the surface of each element after discharge. The observed value of the toe voltage was independent of the initial surface potential of the element.

The results are presented in Table I below.

TABLE I

| Element | Electron-transport Agent | $V_O$ (V) | E (50% $V_O$) (ergs/cm²) | DD (V/s) | $V_{toe}$ (V) |
|---|---|---|---|---|---|
| 1 Control | 4-dicyanomethylene-2-phenyl-6-(4-tolyl)-4H-thiopyran-1,1-dioxide | 80 70 | 16.4 21.2 | <0.1 | 23 |
| 2 Compound (2) | 4-dicyanomethylene-2-(2-thienyl)-6-phenyl-4H-thiopyran-1,1-dioxide | 80 70 | 5.2 5.6 | 0.5 | 19 |
| 3 Compound (3) | 4-dicyanomethylene-2,6-di-(2-thienyl)-4H-thiopyran-1,1-dioxide | 80 70 | 14.8 17.2 | 1.1 | 20 |
| 4 Compound (4) | 4-dicyanomethylene-2-(3-thienyl)-6-phenyl-4H-thiopyran-1,1-dioxide | 80 70 | 9.6 12.0 | 0.2 | 20 |
| 5 Compound (5) | 4-dicyanomethylene-2,6-di-(3-thienyl)-4H-thiopyran-1,1-dioxide | 80 70 | 13.2 16.0 | 0.5 | 19 |
| 6 Compound (6) | 4-dicyanomethylene-2-(2-furanyl)-6-phenyl-4H-thiopyran-1,1-dioxide | 30 20 | 5.3 6.7 | 1.0 | 5 |
| 7 Compound (7) | 4-dicyanomethylene-2,6-di-(2-furanyl)-4H-thiopyran-1,1-dioxide | 80 70 | 4.5 5.2 | 3.5 | 6 |

The data in Table I show that the electrophotographic elements containing compounds (2), (3), (4), (5), (6) and (7) of the invention had higher sensitivity, or speed, than the control, as is evident from their lower E (50% $V_o$) values. In addition, the elements containing electron-transport agents of the invention had good dark decay properties and good toe voltages.

EXAMPLE 5

Structure, preparation, and performance of electrophotographic elements from compounds (2), (4), (6), and (8) and mixtures thereof A charge-generation layer (CGL) on a conductive support was prepared as in Example 4. Coating solutions for forming a charge-transport layer (CTL) comprising 10 weight percent solids in dichloromethane containing a small amount of DC-510 ® siloxane coating aid (from Dow Corning) were then prepared. The solids comprised the electron-transport agent(s) of the invention and a polymeric binder comprising a polyester formed from 4,4'-(2-norbornylidene) diphenol and terephthalic acid: azelaic acid (40:60 molar ratio). The concentrations of electron-transport agents were as noted in Table II. Each solution was coated with a doctor blade on the conductive support containing the CGL and dried to form a CTL on the CGL. The combined thickness of the CGL and CTL was about 10 μm.

A control coating was prepared in the same manner, using the electron-transport agent 4-dicyanomethylene-2-phenyl-6-(4-tolyl)-4H-thiopyran-1,1-dioxide (Compound I-A of U.S. Pat. No. 5,013,849), which is not of the invention.

Each of the electrophotographic elements so prepared was corona-charged to a positive potential. Dark decay was measured from the slope of a voltage versus time plot just prior to exposure for each element. Each element was exposed through the outer surface of the CTL to radiation at a wavelength of 830 nm and at a rate of 2 ergs per cm² of element surface per second to generate electron/hole pairs in the CGL, and the values for $E(50\% V_o)$ were measured. The results are given in Table II.

TABLE II

| Element | Electron-transport Agents (weight % in CTL) | $V_O$ (V) | E (50% $V_O$) (ergs/cm²) | DD (V/s) |
|---|---|---|---|---|
| 1 Control | Compound 1-A of U.S. Pat. No. 5,013,849 (15%) | 490 | 9.3 | 25 |
| 2 | Compound (4) (15%) | 500 | 10.5 | 20 |
| 3 | Compound (6) (14%) | 410 | 14 | 25 |
| 4 | Compound (6) (20%) | 500 | 21 | 20 |
| 5 | Compound (8) (20%) | 500 | 14 | 13 |
| 6 | Compound (2) (6.7%) Compound (4) (6.7%) Compound (8) (7.6%) | 510 | 9.4 | 30 |
| 7 | Compound (2) (10%) Compound (4) (10%) Compound (8) (11%) | 410 | 6.8 | 30 |

As shown by the data of Table II, Element 5, which contained compound (8) of the invention, exhibited especially desirable dark decay properties. In addition, the elements containing ternary mixtures of compounds (2), (4), and (8) of the invention displayed good electrophotographic sensitivity.

EXAMPLE 6

Measurement of electron mobility in coating of compound (2)

A solution of 42 mg of compound (2) and 168 mg of the polymeric binder poly[(4,4'-norbornylidene) diphenylene terephthalate-co-azelate] in 2 mL of dichloromethane was coated in a dry nitrogen atmosphere, using a 125-μm doctor blade, on a CGL coated on a conductive support. The support/CGL was a sheet of nickel-coated poly(ethylene terephthalate) with a very thin (ca 0.02 μm) overcoat of poly(acrylonitrile-co-vinylidene chloride), upon which was deposited a vacuum-sublimed thin layer of bromoindium phthalocyanine (described in U.S. Pat. Nos. 4,666,802 and 4,727,139) having a thickness of less than 1 μm and an optical density at 780 nm of 0.7. The coating of (2) on the support/CGL had, after drying for 2 days at 40° C., a thickness of about 5.7 μm.

The above-described procedure was used to prepare a control coating containing, at the same molar concentration as compound (2), the electron-transport agent 4-dicyanomethylene-2,6-diphenyl-4H-thiopyran-1,1-dioxide (compound 3 of U.S. Pat. No. 4,514,481, incorporated herein by reference). The dried control coating had a thickness of about 6.2 μm.

Multiple gold dots, each approximately 5 mm in diameter and 500 angstroms thick, were deposited on approximately 6-cm² samples of the coatings of compound (2) and the control compound. To establish contact with the conductive nickel layer, a carbon-containing conductive lacquer was applied to the edge of the samples, and the dried lacquered edge was pressed into contact with a steel plate. Contact to the gold dot was made by an indium-coated phosphor bronze tine. The thickness of the samples was determined by measuring the area of the gold dot and the capacitance between it and the nickel layer, assuming a relative dielectric constant of 3.0.

Time-of-flight measurements were made by connecting a sample to a high-voltage power supply via the steel plate and via the phosphor bronze tine through a current-sensing resistor to ground. Any current through the sample produced a proportional voltage across the resistor, which was amplified by a PAR 113 pre-amp and recorded by a SONY/Tektronix 390AD ® digitizer. The record was then analyzed by computer. Flash illumination was provided by a flash lamp, a filter passing light of wavelengths above approximately 540 nm, and neutral-density filters to adjust light intensity.

During application of a voltage, the sample was irradiated for approximately 1 microsecond. The resulting photocurrent typically exhibited an early peak and rapid decline to a plateau, followed by a shoulder and fall-off towards zero. The shoulder was identified as the time required for electrons to cross the sample, i.e., the transit time. The velocity of the electrons was computed as the thickness of the layer divided by the transit time. Electron mobility was determined by dividing this velocity by the electric field strength.

At a field strength of $2 \times 10^5$ V/cm, the control sample containing the electron-transport compound of the prior art exhibited an electron mobility of $2.4 \times 10^{-8}$ cm²/V-sec. At the same field strength, the sample containing compound (2) of the present invention showed comparable electron mobility, $2.6 \times 10^{-8}$ cm²/V-sec.

EXAMPLE 7

Structure, preparation, and performance of electrophotographic elements from compound (6) and mixtures of compounds (2), (4), and (8)

A charge-generation layer (CGL) containing bromoindium phthalocyanine on a conductive support was prepared as in Example 6. Coating solutions for forming a charge-transport layer (CTL) were prepared and coated with a doctor blade on the CGL/support as described in Example 5. The concentrations of electron-transport agents were as noted in Table III.

Each of the elements was corona-charged to a positive potential. Dark decay was measured as previously described in Example 5. Electrophotographic sensitivity was determined by exposing each element to radiation at a wavelength of 780 nm at a rate of 2 ergs per cm² of surface per second and measuring the E (50% $V_o$) values. The results are given in Table III.

TABLE III

| Element | Electron-transport Agents (weight % in CTL) | $V_O$ (V) | E (50% $V_O$) (ergs/cm²) | DD (V/s) |
|---|---|---|---|---|
| 1 | Compound (6) (14%) | 470 | 15 | 25 |
| 2 | Compound (2) (6.7%) Compound (4) (6.7%) Compound (8) (7.6%) | 410 | 7.4 | 35 |
| 3 | Compound (2) (10%) Compound (4) (10%) Compound (8) (11%) | 250 | 3.9 | 25 |

The data in Table III show that compound (6) of the invention functioned as an electron-transport agent in an electrophotographic element. The elements containing ternary mixtures of compounds (2), (4), and (8) of the invention exhibited very good sensitivity.

The invention has been described in detail with particular reference to preferred embodiments thereof, but it will be understood that variations and modifications can be effected within the spirit and scope of the invention.

What is claimed is:

1. An electrophotographic element comprising an electrically conductive layer, a charge-generation layer, and a charge-transport layer containing an electron-transport agent having the structure

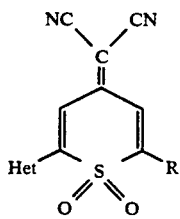
(I)

wherein Het is a substituted or unsubstituted heterocyclic ring system containing at least one 5-membered aromatic heterocyclic ring; and R is an alkyl, aralkyl, or cycloalkyl group of 1 to about 10 carbon atoms, or an aryl group of 6 to about 12 carbon atoms, or a substituted or unsubstituted heterocyclic ring system containing at least one 5-membered aromatic heterocyclic ring.

2. The electrophotographic element of claim 1 wherein R is aryl and Het is thienyl or furanyl.

3. The electrophotographic element of claim 2 wherein R is phenyl and Het is 2-thienyl, 3-thienyl, or 2-furanyl.

4. The electrophotographic element of claim 2 wherein R is 4-ethylphenyl and Het is 5-methyl-2-thienyl.

5. The electrophotographic element of claim 1 wherein R is 3-thienyl and Het is 2-thienyl.

6. The electrophotographic element of claim 1 wherein R and Het are the same.

7. The electrophotographic element of claim 6 wherein R and Het are both 2-thienyl, 3-thienyl, or 2-furanyl.

8. The electrophotographic element of claim 1 wherein said charge-transport layer comprises a vacuum-deposited electron-transport agent.

9. The electrophotographic element of claim 1 wherein said charge-transport layer comprises an electron-transport agent and a polymeric binder.

* * * * *